United States Patent [19]

Lambert

[11] Patent Number: 4,940,900

[45] Date of Patent: Jul. 10, 1990

[54] METHOD AND APPARATUS FOR DETERMINING THE FLOCCULATION THRESHOLD OF A PETROLEUM PRODUCT

[75] Inventor: Didier C. Lambert, Lavera, France

[73] Assignee: BP Oil International Limited, London, England

[21] Appl. No.: 233,196

[22] Filed: Aug. 17, 1988

[30] Foreign Application Priority Data

Aug. 18, 1987 [FR] France ................... 87 11687

[51] Int. Cl.$^5$ .......................................... G01N 21/59
[52] U.S. Cl. .............................. 250/343; 250/227.11
[58] Field of Search .............................. 250/343, 227

[56] References Cited

U.S. PATENT DOCUMENTS

| | | | |
|---|---|---|---|
| 4,236,076 | 11/1980 | Judge et al. ................... | 250/347 |
| 4,530,234 | 7/1985 | Cullick et al. ................... | 73/53 |
| 4,628,204 | 12/1986 | Maes ................... | 250/343 |
| 4,641,973 | 2/1987 | Nestler et al. ................... | 250/343 |
| 4,707,134 | 11/1987 | McLachlan et al. ................... | 250/227 |

FOREIGN PATENT DOCUMENTS 2566909 6/1984 France .
2578979 9/1986 France .

OTHER PUBLICATIONS

Fraim et al., "Natural Gas Heating Value Determination Using Infrared Calorimeter" American Gas Association (undated).

Fredericks et al., "Materials Characterization Using Factor Analysis FT-IR Spectra. Part 1:Resutls", vol. 39, No. 2, Applied Spectroscopy (1985).

Briot, "Analyse en ligne par absorption infrarouge Essai de prospective", 12/1/67 pp. 71-78 *Measures Regulation-Automatisme*.

Fredricks et al., "Rapid Coal Characterization by FT-ir Spectroscopy", Jan. '84, 139-141 *Fuel*.

Fredricks et al., "Material Characterization Using Factor Analysis of FT-ir Spectra. Part 2: Mathamatical and Statistical Considerations", pp. 311-316 (1985) vol, 39, No. 2, *Applied Spectroscopy*.

Primary Examiner—Constantine Hannaher
Assistant Examiner—J. Eisenberg
Attorney, Agent, or Firm—Larry W. Evans; David J. Untener; Michael F. Esposito

[57] ABSTRACT

The flocculation threshold of a petroleum product containing asphaltenes is measured by measuring the radiation in the near infrared transmitted through a sample of the product in solution in a solvent in relation to the quantity of precipitant continuously added to the sample.

13 Claims, 2 Drawing Sheets

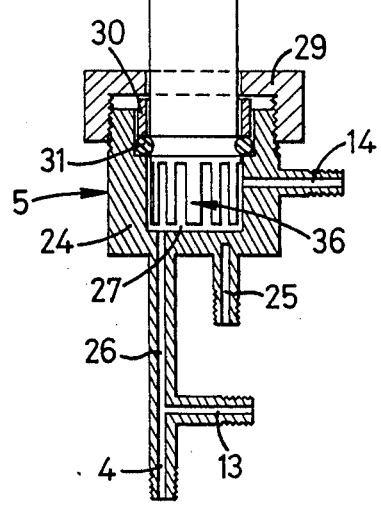
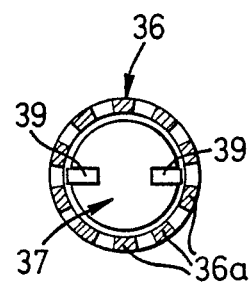

METHOD AND APPARATUS FOR DETERMINING THE FLOCCULATION THRESHOLD OF A PETROLEUM PRODUCT

This invention relates to the measurement of the flocculation threshold of a petroleum product containing a certain proportion of asphaltenes. Determining the flocculation threshold makes it possible to obtain the xylene equivalent, precipitablity and stability values as well as the solvent power of the product.

Asphaltenes may be defined as those components of a crude oil, fuel oil or distillation residue which are insoluble in heptane at its boiling-point and soluble in benzene at its boiling-point.

The flocculation threshold is usually defined as the minimum quantity of an alkane such as heptane which must be added to a specific quantity of the petroleum product at a specific dilution in order to initiate flocculation. The article by G. Hotier and M. Robin in the French Petroleum Institute Journal (volume 38 no. 1 Jan./Feb. 1983) gives details of these definitions and proposes an experimental measuring device which detects the radiation transmitted in the near infrared. The device uses a circulating cell containing a quantity of a petroleum sample diluted by a solvent and a continuous injection device which allows increasing quantities of the flocculating agent to be gradually added. The measurement is made by detecting the transmission of near infrared radiation in a cell having a mirror, the light being conducted and returned by a Y-shaped optical fibre device.

This laboratory device suffers from the disadvantage of having to make measurements with a variable dilution level, since the volume of the initial petroleum residue sample remains constant whatever volume of focculating agent is added.

The present invention relates to a method and apparatus for measuring the flocculation threshold which may be used not only in the laboratory but also on-line for industrial plant process control. The invention enables the flocculation threshold of a petoleum product to be determined at constant dilution.

According to the present invention there is provided a method for measuring the flocculation threshold of a petroleum product containing asphaltenes which method comprises measuring the radiation in the near infrared transmitted through a sample of the product in solution in a solvent in relation to the quantity of precipitant continuously added to the sample.

According to the invention, the solvent and the precipitant are continuously blended at variable concentrations. The solvent, precipitant blend and the product are continuously fed, in constant proportions into a homogenizing chamber. The transmitted radiation intensity in the near infrared is continuously measured downstream of the homogenizing chamber.

To obtain results at different pressures, the pressure in the homogenizing chamber may also be varied by around 15 bar. similarly, to obtain results at different temperatures, the pump, the various lines and the homogenizing chamber may be maintained at a constant temperature that may vary, for example, between 20° and 150° C.

The apparatus according to the invention which makes it possible to carry out the method for determining flocculation, comprises a blending and homogenizing chamber comprising means for agitation and a near infrared radiation sensor, preferably the optical type. The system comprises a variable delivery pump for the solvent and another variable delivery pump for the precipitant. A programming device controls the respective deliveries of the two pumps, while keeping the total delivery of solvent and precipitant constant. The device additionally comprises a third pump for the product to be treated, the blending and homogenizing chamber being fed with both the product and the solvent and precipitant blend at a dilution rate which is constant. The blending and homogenizing chamber comprises a means for homogenization able to dissolve the product and homogenize the blend. A sensor is fitted downstream of the homogenizing chamber on an outlet line.

The homogenizing chamber is preferably fitted with an axial homogenizing rotor which fills most of its internal space, leaving virtually no dead volume. The product and solvent/precipitant blend is preferably fed to the front of the homogenizing chamber, while the dissolved, homogenized blend is removed by an outlet in the side wall.

A pressure regulating device is preferably fitted on the outlet line, downstream of the sensor, thus making it possible to vary the pressure in the measuring device and in particular to maintain the pressure at a sufficiently high level for the precipitant, for example hetane, to remain liquid.

The sensor preferably comprises a near infrared optical fibre source, an aperture which allows the homogenized blend leaving the blending chamber to pass through and a sensing optical fibre located on the other side of the aperture opposite the source.

To enable measurements to be made as a function of temperature, the homogenizing chamber comprises means for keeping it a constant temperature while allowing this temperature to be varied. Similarly, the product pump may also be kept at the same temperature so as to promote the regularity of the product flow.

A gear pump is preferably used for high viscosity products, which are almost solid at ambient temperature.

If a measurement is to be made at a different dilution level, the product flow may be varied by using a variable delivery pump. The same result may also be obtained by keeping the product flow constant and varying the delivery of the blend formed by the solvent and the precipitant.

The system preferably comprises a control computer receiving data directly from the programming device and transmitted radiation sensor, thus making it possible to control the pump shutdown automatically as soon as the asphaltene flocculation threshold is detected and to supply the desired results directly. The computer is able to control the whole system, in particular the pump delivery, the temperature of the various components and the pressure within the system.

The invention is illustrated with reference to FIGS. 1-3 of the accompanying drawings wherein:

FIG. 2 is a sectional elevation view of the blending and homogenizing chamber; and FIG. 3 is a section of the homogenizing rotor to be fitted in the homogenizing chamber.

Figure 1:
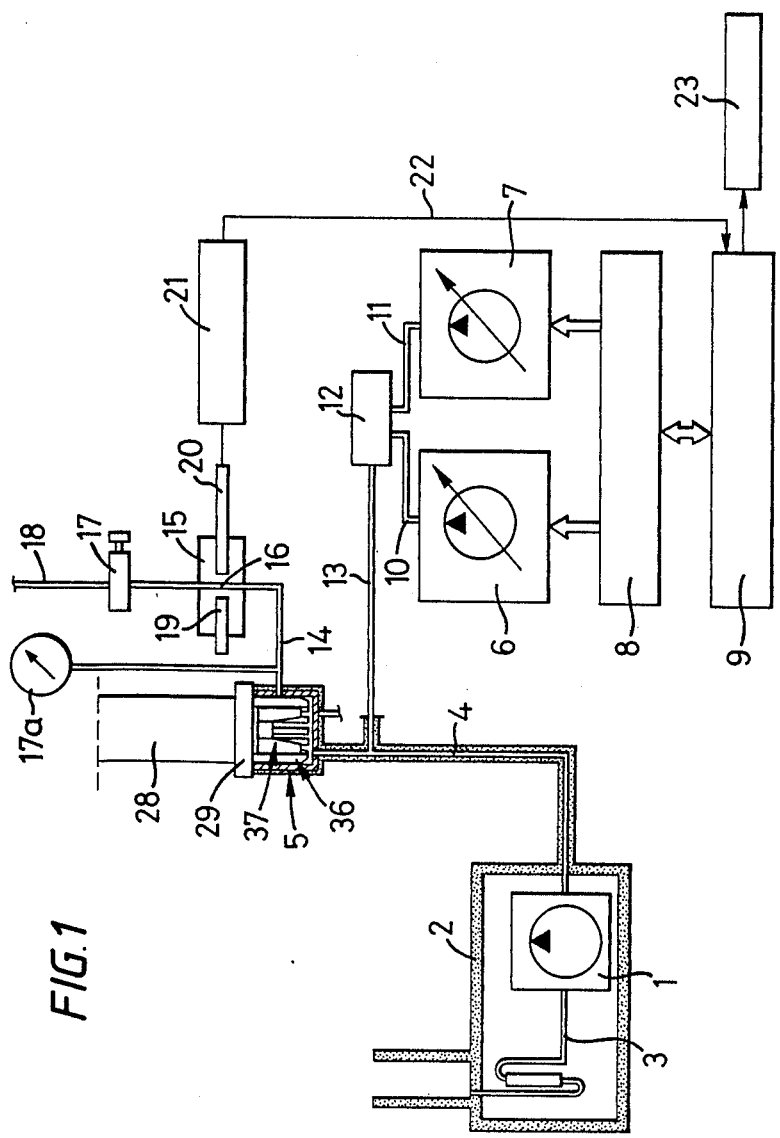
FIG. 1 is a schematic view of the various components of the measuring system.

The system as illustrated in FIG. 1 comprises a fixed delivery pump 1 maintained at high temperature inside a thermostatically controlled chamber 2. The pump 1, preferably a gear pump is used to pump a fuel oil fed from the storage tank (not shown in the illustration) by means of a feed line 3. The pumped product is fed through line 4 held at a constant temperature until it reaches a blending and homogenizing chamber 5 also held at constant temperature which may be adjusted. The system further comprises a first variable delivery pump 7 for a flocculating precipitant such as heptane. The two pumps 6 and 7 are measuring pumps, the delivery adjustment of which is controlled by a programming device 8 in turn controlled by a microcomputer 9. The programming device 8 is able to vary the respective concentrations of solvent and precipitant linearly and continuously by acting on the variable delivery of the two pumps 6 and 7 in such a way that the total delivery of the blend solvent and precipitant from the two pumps 6 and 7 is kept constant. The two lines 10 and 11 leading from the two pumps 6 and 7 respectively meet at 12 in a single blend feed line 13. Line 13, kept at constant temperature, is connected to line 4 feeding the product from pump 1. The product and the blend formed by the solvent and the precipitant are blended and homogenized in the chamber 5 which comprises a homogenizing device formed by a fixed cage 36 with vertical bars and a high speed rotor 37 arranged inside cage 36. The blend homogenized at constant temperature inside the chamber 5 leaves the chamber through line 14 which is connected to the measuring cell 15 which has an opening 16 between two parallel transparent slides through which the blend for analysis passes. A pressure control device 17 is fitted on the outlet line 16 downstream of the measuring cell 15. The pressure in the system is measured by a pressure gauge 17a. The measuring cell comprises a near infrared radiation conducting optical fibre 19 and a sensing optical fibre 20 positioned on the other side of window 16 and connected by means of a amplifier 21 to the computer 9 via connection 22. The results processed by the computer 9 are obtained automatically on a display printing device 23. As the programmer 8 is also connected to the recorder via the computer 9, it is possible to obtain directly, throughout the measuring process, curves for the concentration of xylene and heptane an the result of near infrared radiation sensing in the measuring cell 15. Thus, as soon as a precipitate appears in the measuring cell 15, this is sensed by a change in the slope of the transmitted intensity curve, and the exact percentages of solvent and precipitant for the flocculation threshold may be determined. As soon as the flocculation threshold is sensed, the microcomputer 9 may order the shutdown of the pumps 6 and 7.

The measurement is made by determining at each moment the xylene eqivalent as a function of the percentage of the solvent/precipitant blend which makes it possible to determine a threshold of precipitablility of the asphaltenes in the product in relation to a constant quantity of a blend in variable proportions of the solvent such as xylene and the precipitant such as heptane. The dilution in the blending and homogenizing chamber 5 is held constant throughout the measurement.

If a measurement is to be made at a different dilution level, it is possible to vary the delivery of the pump 1 by using a variable delivery pump. It is also possible to vary the level of dilution while keeping the product delivery constant and varying the total delivery from the two pumps 6 and 7.

The blending chamber as illustrated in FIG. 2 is represented in diagram form with a thermostatically controled thick outer wall enclosure 24. The temperature may be kept constant by circulating liquid as represented by the hatchings on FIG. 2 within the wall of the blending chamber 5 and around the feed lines 4 and 13. The temperature to be regulated is measured by thermocouples set into the shaft 25. It will be noted that line 26 supplying the blend of residue from line 4 and the xylene and heptane from line 13 enters through its base front wall. The line 14 on the other hand leaves through the side wall of internal chamber 27.

The homogenizing device is fitted to the end of rod 28 which penetrates inside the column 27 of the chamber 5. The rod 28 is fitted inside a threaded cover 29 screwed on the outer wall of the chamber 5 and making contact with a spacer 30 which exerts pressure on the o-ring 31 thus ensuring a seal for the internal chamber 27. The internal chamber 27 is filled by the cage 36 fitted fixed to the inside of the said internal chamber 27. The cage 36 comprises a number of vertical risers 36a, the free ends of which are close to the bottom of the chamber 5. Inside the cage 36 is fitted an axial rotor 38, not shown on FIG. 2 but in the section in FIG. 3, which comprises two blades (39) directly opposite each other. The rotor 37 is rotated inside the cage 36 which causes homogenization of the blend of product and the mixture of solvent and precipitant entering by line 26. A homogenizer sold under the trade name ULTRA TURAX may be used. In this the overall dimensions of the cage 36 correspond closely to those of the internal volume 27 of the chamber 5 so that there is practically no dead space left inside the chamber. In these conditions the product leaving by line 14 is completely homogenized and the measurement in the cell 15 is made on a completely homogenous product.

The temperature in the blending and homogenizing chamber 5 may be held at a temperature of up to around 150° C. The pressure in the system may also be kept at a high level, sufficient to ensure that the heptane remains liquid.

The method and apparatus according to the invention make it possible to control and optimize visbreaking operations not only off-line in the laboratory but also on-line if the measuring system is installed at a pilot plant or industrial unit and used directly for process control. The invention may also be used to control and correct the stability of fuel oils and to control the transporting of crude petroleum products in pipelines by determining the characteristics of blends carried at any time. The invention may also be used to control and optimize deasphalting processes.

I claim:

1. A method for determining the flocculation threshold of a petroleum product containing asphaltenes by measuring the near infrared radiation transmitted through a sample of the product in solution in a solvent in relation to the quantity of precipitant continuously added to the sample, characterized in that:

a blend of solvent and precipitant is continuously formed at variable concentrations;

the blend and the petroleum product are fed in constant proportions into a homogenizing chamber; and the near infrared radiation transmitted through the homogeneous product is measured continuously downstream of the homogenizing chamber.

2. A method according to claim 1 characterized in that the pressure in the homogenizing chamber may be varied in order to obtain a measurement at different pressures.

3. A method according to claim 1, characterized in that the product and the homogenizing chamber are kept at a constant temperature which may be varied in order to obtain a measurement at different temperatures.

4. Apparatus for measuring the flocculation threshold of a petroleum product containing asphaltenes by measuring the near infrared radiation transmitted through a sample of product in solution in a solvent in relation to the quantity of procipitant continuously added to the sample, comprising a blending chamber (5) containing means for agitation (39), and a near infrared radiation sensor (15) characterized in that it comprises:

(a) a variable delivery pump (6) for the solvent, a variable delivery pump (7) for the precipitant and a programming device (8) controlling the respective deliveries of the two pumps (6) and (7) while keeping the total delivery of the blend of solvent and precipitant constant;
  (b) and pump (1) for the product;
  (c) a homogenizing chamber (5) fed with both the product and the blend of solvent and precipitant and having homogenizing means (36, 37) able to dissolve the petroleum product and homogenize the blend;
  the sensor (15) being situated downstream of the homogenizing chamber on an outlwt line (14).

5. Apparatus according to claim 4 characterized in that the homogenizing chamber is occupied by an axial homogenizing rotor (36, 37), the petroleum product and the solvent and precipitant blend entry being in front of the chamber and the blend exit being in the side wall.

6. Apparatus according to claim 4 characterized in that a pressure regulating device (17) is fitted on the outlet line (14) downstream of the sensor (15).

7. Apparatus according to claim 4 characterized in that the sensor (15) comprises an optical fibre (19) conducting in the near infrared spectrum, an aperture (16) through which the blend passes and a sensing optical fibre (20) on the other side of the aperture.

8. Apparatus according to claim 4 characterized in that the homogenizing chamber (5) and the product pump (1) are thermostatically controlled.

9. Apparatus according to claim 4 characterized in that the product pump (1) is a gear pump.

10. Apparatus according to claim 4 characterized in that the product pump (1) is a variable delivery pump which makes it possible to measure the flocculation threshold in relation to the the dilution level.

11. Apparatus according to claim 4 characterized in that it comprises a control computer (9) which receives data directly from the programming device (8) and the sensor (20) to control the shutdown of the pumps (6, 7) as soon as the asphaltene flocculation threshold appears and supply the results immediately.

12. A method for determining the flocculation threshold of a petroleum product containing asphaltenes by measuring the near infrared radiation transmitted through a sample of the product in solution in a solvent in relation to the quantity of precipitant continuously added to the sample, characterized in that:

a blend of solvent and precipitant is continuously formed at variable concentrations;
  the blend and the petroleum product are fed in constant proportions into a homogenizing chamber;
  the pressure in the homogenizing chamber may be varied in order to obtain a measurement at different pressures; and
  the near infrared radiation transmitted through the homogenous product is measured continuously downstream of the homogenizing chamber.

13. Apparatus for measuring the flocculation threshold of a petroleum product containing asphaltenes by measuring the near infrared radiation transmitted through a sample of product in solution in a solvent in relation to the quantity of precipitant continuously added to the sample, comprising a blending chamber containing means for agitation, and a near infrared radiation sensor characterized in that it comprises:

(a) a variable delivery pump for the solvent, a variable delivery pump for the precipitant and a programming device controlling the respective deliveries of the two pumps while keeping the total delivery of the blend of solvent and precipitant constant;
  (b) a pump for the product;
  (c) a homogenizing chamber fed with both the product and the blend of solvent and precipitant and having an axial homogenizing rotor able to dissolve the petroleum product and homogenize the blend;
  the sensor being situated downstream of the homogenizing chamber on an outlet line (14).

* * * * *

UNITED STATES PATENT AND TRADEMARK OFFICE
CERTIFICATE OF CORRECTION

PATENT NO. : 4,940,900

DATED : July 10, 1990

INVENTOR(S) : Didier Charles Lambert

It is certified that error appears in the above-identified patent and that said Letters Patent is hereby corrected as shown below:

At column 3, line 6, after "delivery" there should have been inserted --pump for a solvent and a second variable--.

Signed and Sealed this

Twenty-ninth Day of September, 1992

Attest:

DOUGLAS B. COMER

*Attesting Officer*  *Acting Commissioner of Patents and Trademarks*